United States Patent [19]

Blake et al.

[11] 4,398,910

[45] Aug. 16, 1983

[54] WOUND DRAIN CATHETER

[76] Inventors: Larry W. Blake, 2885 Regis La., Costa Mesa, Calif. 92626; Ervin R. Harvel, 23991 Lindley, Mission Viejo, Calif. 92675; Duane R. Mason, 31 Farragut, Irvine, Calif. 92664; George M. Wright, 24145 Puerta Deluz, Mission Viejo, Calif. 92675

[21] Appl. No.: 238,640

[22] Filed: Feb. 26, 1981

[51] Int. Cl.³ .............................................. A61M 27/00
[52] U.S. Cl. ..................................... 604/93; 604/266; 604/280
[58] Field of Search .......................... 128/348–350 R, 128/347; 604/93, 266, 280, 283

[56] References Cited

U.S. PATENT DOCUMENTS

| 3,582,234 | 6/1971 | Isreeli | 417/53 |
| 3,599,641 | 8/1971 | Sheridan | 128/348 |
| 3,623,484 | 11/1971 | Schulte | 128/350 R |
| 3,630,206 | 12/1971 | Gingold | 128/349 B |
| 3,993,080 | 11/1976 | Loseff | 128/350 R |

FOREIGN PATENT DOCUMENTS

| 2240026 | 3/1975 | France | 128/350 R |
| 105038 | 3/1917 | United Kingdom | 128/350 R |

Primary Examiner—Dalton L. Truluck
Attorney, Agent, or Firm—Knobbe, Martens, Olson & Bear

[57] ABSTRACT

The wound drain catheter of the present invention is comprised of a drain portion connected to an outflow tube portion. The drain portion comprises a central core with plural T-shaped members projecting therefrom to form plural lumens having respective longitudinal grooves for fluid communication with the wound. This drain has a uniform cross-sectional area and is preferably made from a silicone elastomer having a durometer shore between 40 and 70 shore A. Such uniform cross-sectional area provides added strength to prevent the drain from breaking during its removal from the patient's body, and the silicone elastomer provides sufficient elasticity to permit the cross-sectional area of the drain to decrease by at least 30 percent when a pulling force is applied thereto, thereby reducing the gripping force of tissue surrounding the wound.

32 Claims, 12 Drawing Figures

WOUND DRAIN CATHETER

BACKGROUND OF THE INVENTION

The present invention relates to wound drain catheters for draining fluid from, or supplying medication to, a closed deep wound. This invention also relates to a method for attaching a stainless steel trocar to a silicone outflow tube of a catheter.

Virtually all wound drain catheters used in closed wounds comprise a drain portion for fluid communication with the wound and an outflow or extension tube portion. Typically, the tube portion is connected to a vacuum supply after (a) the drain has been placed in the wound and (b) the wound, or surgical incision, has been closed. The most common type of prior art drain comprises a length of tubing which is perforated by forming spaced apertures through the tubing wall. These apertures are usually in opposed pairs and, while the spacing between aperture pairs may vary, such aperture pairs are typically spaced by a distance equal to approximately twice the diameter of the tubing. One major problem with these prior art drains is that wound debris, such as clots, may block a number of the apertures, thereby substantially reducing the effectiveness of the drain. A more serious problem is that, as the wound heals, tissue tends to grow into the apertures. Such tissue growth not only blocks the apertures, but, in addition, when the physician removes the drain by applying a strong pulling force on the catheter, the portion of tissue that has grown into the apertures will be literally ripped from the patient's body. This causes severe discomfort to the patient and retards the healing process. Moreover, if the tissue growth into the aperture is extensive, the drain may break when the physician attempts to remove it, thereby leaving a portion of the drain in the patient's body. If this occurs, additional surgery may be required to extract the broken portion of the drain.

A further disadvantage of prior art perforated drains is that their apertures tend to structurally weaken the drain. Since the cross-sectional area of the drain body is reduced at each of the apertures, the apertures create weak points in the drain tube wall. Further, when tensile forces are applied to the drain, the tensile stresses at the top and bottom of an aperture are particularly high, since the tensile forces are unable to pass across the aperture. That is, the material adjoining the aperture must carry the stresses which are unable to bridge the aperture in addition to its normal share of the stress. Thus, an area of discontinuity, such as an aperture, is commonly referred to as a "stress raiser". Perforated drains, therefore, are much weaker than their drain body cross-sectional area suggests, since each of the perforations creates a "stress raiser".

Moreover, since perforated drains have a tubular structure, they tend to kink when bent or squeezed, as by movement of the patent. If this occurs, the effectiveness of the drain may be substantially impaired, thereby warranting premature removal of the drain.

Wound drains made from a silicone elastomer are usually preferable to drains made from other materials, since silicone is highly biocompatible, soft, and flexible. In contrast, materials such as PVC are more rigid, and therefore, tend to irritate the wound. This causes substantial discomfort to the patient and inhibits healing. Further, PVC is less biocompatible than silicone. Materials such as natural rubber are seldom ued for closed wound drains because of toxicity problems. Thus, silicone is typically the most advantageous material for closed wound drains. However, silicone is not as strong as PVC, and thus, it tends to rupture more easily during drain removal from a closed, deep wound. This has limited the usefulness of silicone drains in many applications.

For the purpose of illustrating the structural characteristics of a typical perforated drain, one exemplary form of prior art perforated drain, in common and widespread use, will be described. This exemplary drain has an outside diameter D, an inside diameter about one-half D, opposed pairs of perforations having a diameter of about one-half D, and an axial spacing of about 2D. Using well known mathematical formulas, it may be found that this exemplary drain has a lumenal drainage area of $0.196D^2$, a tissue contact drainage area of $0.196D^2$ units per unit D of length, and a drain body cross-sectional area of $0.0307D^2$ at each of the aperture pairs. These parameter values will be subsequently compared to corresponding parameter values for the present invention, in order to contrast the significant improvements in drain effectiveness and strength provided by the present invention.

Non-perforated drains have been proposed for use in shallow surface wounds, such as those created by plastic surgery. For example, a drain of this type is illustrated in U.S. Pat. No. 3,860,008, issued to Miner et al. Another similar type of non-perforated drain is disclosed in U.S. Pat. No. 105,038 (British), issued to Liddell. Both of these drains, however, are specifically designed to be patent to the atmosphere, rather than to an outflow tube. Thus, the drain is always exposed to infection causing organisms. Consequently, the problems associated with closed, deep wounds, such as providing an aseptic environment, and providing safe, reliable drain removal while maintaining drain effectiveness, are not addressed.

Several techniques may be used to insert a wound drain catheter in the patient's body. For example, a surgeon may simply place the drain portion and a small part of the outflow tube portion in the wound, close the incision, and suture around the outflow tube portion. This technique is somewhat unsatisfactory, since it is difficult to completely seal the area around the outflow tube by suturing, and thus, the wound may become infected. A more satisfactory technique is to pass a trocar, preattached to the end of the outflow tube, through healthy tissue by entering the patient's body at a point within the wound and exiting at a point adjacent to the wound. The surgeon pulls the outflow tube portion through the tissue with the trocar until the catheter is properly positioned, with the drain in the wound. Since the outflow tube exits the body at a point adjacent the wound, the wound can be completely closed by suturing, thereby reducing the risk of infection.

When outflow tubes made from silicone are used, the trocar and the tube sometimes separate, leaving the end of the outflow tube in the patient's body. If this occurs, the outflow tube must be removed and the procedure repeated. Such separation is due to the difficulty of attaching the trocar to the outflow tube. Typically, the end of the trocar includes a connector portion having annular ridges which grippingly engage the inner surface of the outflow tube. However, since a silicone catheter tube is soft and flexible, it tends to easily detach itself from the annular ridges when subjected to tensile force. Accordingly, there is a need for an improved method of attaching a silicone catheter tube to a trocar.

SUMMARY OF THE PRESENT INVENTION

The present invention comprises a wound drain which, in comparison with similarly sized prior art drains, has an increased tissue contact drainage area, and an increased lumenal flow drainage area. Thus, the drain of the present invention is substantially more effective than prior art drains. Further, the specific configuration of this drain provides an increased drain body cross-sectional area, and eliminates stress risers (weak points) in the drain body. This makes the drain of the present invention significantly stronger than comparably sized prior art drains, and therefore, it is less likely to break during removal. Moreover, this drain configuration reduces the risk that tissue growth will inhibit removal of the drain. Thus, the drain provides safety, reliability, and effectiveness not found in prior art drains.

The wound drain of the present invention is fluted and, in a first embodiment, comprises a central core with four strut portions projecting radially therefrom. The radial strut portions are of equal size and are spaced at equal angles relative to each other. An overhang portion is provided at the end of each of the four strut portions, thereby forming four T-shaped members. These overhang portions from the periphery of the wound drain, and thus, the overhang portions and strut portions cooperate to form four channels or lumens which extend throughout the length of the drain. Viewed cross-sectionally, the overhang portions cooperate to form a segmented circle having gaps between adjacent overhang portions. The gaps extend longitudinally throughout the length of the drain, and thus, form grooves which permit fluid entry into the lumens.

The grooves may have a width of about 0.05 to 0.2 times the diameter (D) of the drain. Since such width is significantly smaller than the apertures of perforated drains (typically 0.5D), the drain of the present invention is much more effective in preventing the entry of clots or tissue growth into the lumens. However, even though the width of the grooves is relatively small, their combined tissue contact drainage area is about $0.4D^2$ per unit D of length, assuming a groove width of 0.1D. In contrast, the previously described prior art perforated drain has a tissue contact drainage area of only $0.196D^2$ per unit D of length. Thus, the drain of the present invention has about twice the tissue contact drainage area, and therefore, is significantly more effective.

The combined cross-sectional area of the lumens, that is, the lumenal flow drainage area, is equal to the total cross-sectional area of the drain less the drain body cross-sectional area. Thus, as an illustration, if the drain body cross-sectional area is assumed to be $0.411D^2$, the lumenal drainage area is $0.374D^2$. This is about 1.9 times the lumenal flow drainage area ($0.196D^2$) of the previously described perforated drain. Thus, in addition to providing twice the tissue contact drainage area, the fluted drain of the present invention provides nearly twice the lumenal flow drainage area.

This fluted drain is uniform in cross-section throughout its length, and therefore, stress risers and weak points in the drain are eliminated. Further, the above-mentioned drain body cross-sectional area of $0.411D^2$ is about one-third greater than the cross-sectional area of a perforated drain at its opposed aperture pairs. Therefore, in addition to nearly doubling the tissue contact and lumenal flow drainage areas, the drain body cross-sectional area of the present invention is greater by a factor of approximately one-third.

The increased area of the drain body and elimination of stress risers significantly increases the tensile strength of the drain and thereby reduces the risk that the drain might rupture during removal. Since this risk is particularly acute in drains made from a silicon elastomer, the present invention is particularly appropriate for this type of drain. Tests were conducted to compare the tensile strength of a typical, commercially available, 19 French (about 0.25 inch), round, perforated, silicone drain; a 10-mm flat, perforated, silicone drain; and a 19 French, fluted drain, made from a 50 Shore A silicone, and having four lumens. These tests showed that both of the perforated drains ruptured at a tensile force of about 8 to 10 pounds, while the fluted drain ruptured at 22 pounds. Thus, the fluted drain of the present invention has more than twice the tensile strength of comparable perforated silicone drains.

Although the increased tensile strength of the fluted drain provides added protection against a drain breaking off within the patient's body during removal, it is believed that this risk is even further reduced by other characteristics of the present invention. For example, the above-described tensile strength tests also showed that the cross-sectional area of the drain decreases rapidly when a pulling force is applied thereto. Specifically, it has been found that a pull force of only 2 pounds decreases the cross-sectional area of the drain by 50 percent, and that a pull force of 12 pounds decreases the cross-sectional area by 75 percent. A reduction in cross-sectional area of at least 30 percent in response to a two-pound pull force is considered to be advantageous. As the surgeon removes the drain, the pulling force causes it to "neck down", or reduce in cross-sectional area, along its length, thereby relieving the gripping force of the tissue and permitting the drain to be more easily removed. Moreover, since, as described above, the width of the grooves is relatively small, it is unlikely that tissue will grow into the lumenal flow path. However, even if such tissue growth does occur, it is believed that this will not restrict removal of the drain, since any such tissue growth will be along the grooves, and thus, the tissue will simply slide in the grooves when the drain is removed. This minimizes the danger of tissue damage and reduces discomfort to the patient.

Although the above-described drain has four flutes, it will be understood that a different number of flutes may be used. However, it has been found that for drains manufactured from silicon having a durometer shore between 40 and 70 shore A, providing four flutes has significant advantages over more or less members of flutes. For example, drains having more than four flutes require more raw materials for manufacture, and, while extra flutes may add a slight amount of strength, they offer few other advantages. On the other hand, drains having less than four flutes tend to kink easily. Further, they are susceptible to being squeezed or pinched by the movement of surrounding body tissue, thereby rendering them ineffective. It has been found that a three-fluted drain provides some kink resistance, and thus, may be appropriate in some cases. However, drains having less than three flutes are considered to be far less practical, since they are extremely susceptible to squeezing, pinching, and binding, and thus, do not function properly. The four-fluted drain, therefore, provides the most advantageous balance between kink resistance and the amount of raw material needed to form the drain.

In a second embodiment of the present invention, the drain has a somewhat different configuration. Although this drain functions in the same manner as the drain of the first embodiment, its overhand portions, when viewed cross-sectionally, cooperate to form a segmented oval rather than a segmented circle. This drain is particularly appropriate for use between organs, or in other areas where surgeons typically prefer drains having an oval or flat profile. However, like the drain of the first embodiment, the drain of the second embodiment is specifically designed for use in draining closed, deep wounds.

In either embodiment, the drain portion of the catheter is preconnected to the outflow tube portion. This may be accomplished by forming a butt joint between the ends of the drain and tube, and connecting them by a collar. However, since the lumens of the present invention are spaced about the periphery of the drain, rather than at its center, it is possible that the butt joint may close the end of the lumens, thereby prohibiting fluid flow from the drain into the outflow tube. Accordingly, the end of the drain, which is joined to the outflow tube, is undercut to provide a semi-spherical recess for fluid communication between the lumens and the outflow tube. Thus, fluid travels through the lumens, into the semi-spherical recess, and from the semi-spherical recess into the outflow tube. This prevents the butt joint from inhibiting proper operation of the drain.

Another aspect of the present invention relates to a method of attaching a stainless steel trocar to an outflow tube made from a silicone elastomer. The connector portion of the trocar is coated with a primer which creates a bonding surface compatible with both stainless steel and silicone. Since the connector portions of trocars typically have annular ridges, the spaces between the ridges are filled with a silicone adhesive sealant prior to inserting the silicone outflow tube onto the connector portion. This provides a strong bond between the tube and connector portion throughout the length of the connector portion, and insures that the outflow tube will not separate from the trocar when the connector portion is passed through tissue.

BRIEF DESCRIPTION OF THE DRAWINGS

These and other advantages of the present invention are best understood through reference to the drawings in which.

DETAILED DESCRIPTION OF THE PREFERRED EMBODIMENTS

Figure 1:
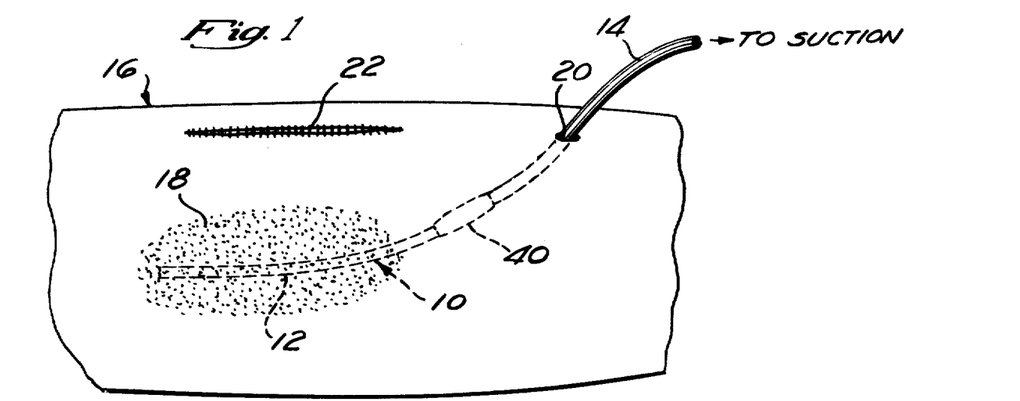
FIG. 1 is a schematic drawing of the wound drain catheter of the present invention placed in a closed, deep wound, showing the drain portion and part of the outflow tube in the patient's body.

Referring to FIG. 1, the wound drain catheter 10 of the present invention includes a flexible drain portion 12 preconnected to a flexible outflow tube portion 14. The drain 12 and a small part of the tube 14 are placed in the patient's body 16 with the drain portion 12 in fluid communication with the wound 18. Preferably, the outflow tube 14 is connected to a sealed, sterilized suction device (not shown) for drawing fluid through the wound drain catheter 10. In addition, it is also preferable that the outflow tube 14 exit the patient's body 16 through an aperture 20 formed in healthy tissue, adjacent to the wound 18. Further, the outflow tube 14 should have a smooth exterior to permit the surface tissue surrounding the aperture 20 to seal against the exterior of the tube 14, and thus, prevent air from passing therebetween. This permits the wound 18 to be completely closed, as by sutures 22, and covered with a dressing (not shown) to form an aseptic barrier, thereby sealing the wound from the atmosphere. Thus, since the drain 12 is patent only to the sterile suction device, and not to the atmosphere, risk of infection is reduced.

Figure 2:
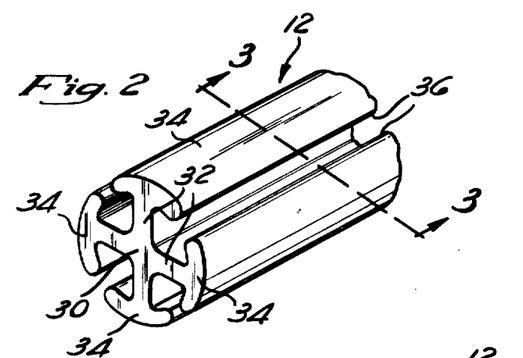
FIG. 2 is a partial perspective view of a first embodiment of the present invention showing a four-lumen, round drain.
Figure 3:
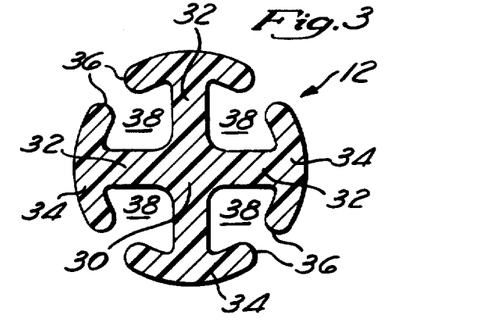
FIG. 3 is a cross-sectional view of the drain of the first embodiment taken along the lines 3—3 of FIG. 2.

The drain of the present invention is fluted, and is preferably radially symmetrical. In a first embodiment, the drain 12 comprises an elongate, cylindrical core portion 30 with four strut portions 32 projecting radially from the core 30 along its longitudinal axis. The radial strut portions 32 are of equal size and are spaced at equal angles relative to each other. Each of the outer ends of the strut portions 32 have respective overhang portions 34 which extend longitudinally throughout the length of the strut portions 32. Viewed cross-sectionally, as best seen in FIG. 3, the overhang portions 34 are thin arcuate members which extend an equal distance on either side of their respective strut portions 32. Thus, the overhang portions 34 and respective strut portions 32 combine to form four T-shaped members. The overhang portions 34 are sized to form a segmented circle at the periphery of the drain 12, with small gaps between adjacent overhang portions 34. Each of these gaps forms a longitudinal groove 36, parallel to the longitudinal axis of the core 30, and extending throughout the length of the drain 12, as shown in FIG. 2. The core portion 30, strut portions 32, and overhang portions 34 cooperate to form plural channels or lumens 38 along the length of the drain 12. The grooves 36 permit fluid communication between a respective one of the lumens 38 and the wound 18 (FIG. 1). Preferably, the width of the grooves 36 is approximately 0.05 to 0.2 times the outside diameter of the drain. This insures adequate tissue contact drainage area while inhibiting tissue growth or entry of debris, such as clots, into the lumens 38.

Figure 4:
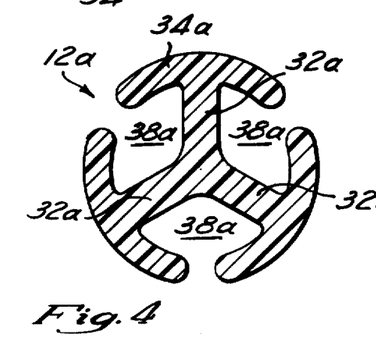
FIG. 4 is a cross-sectional view of a drain similar to the drain of FIGS. 2 and 3, but having three lumens instead of four.

Although the embodiment shown in FIGS. 2 and 3 is described as having four lumens 38, it will be recognized that a different number of lumens 38 may be provided by varying the number of strut portions 32 and respective overhang portions 34. For example, the triple lumen drain 12(a), shown in FIG. 4, utilizes three strut portions 32(a) and three respective overhang portions 34(a) to form three lumens 38(a). Other combinations will be apparent to those skilled in the art. However, for fluted drains manufactured from a 40-70 shore A silicone elastomer, it has been found that the number of lumens provided is critical. For example, drains having less than three lumens are far less practical, since they are extremely susceptible to punching, kinking, and squeezing. Moreover, drains having more than four lumens require additional raw material per unit of length if the T-shaped struts are of a sufficient thickness to provide enough strength to hold their shape. Such a drain would have a reduced lumen sectional area, with few compensating advantages. Further, while three lumen drains provide some kink resistance, it has been found that a four lumen drain provides the most advantageous balance between kink resistance and unit cost of manufacture. Thus, the four-fluted drain is particularly desirable.

Figure 5:
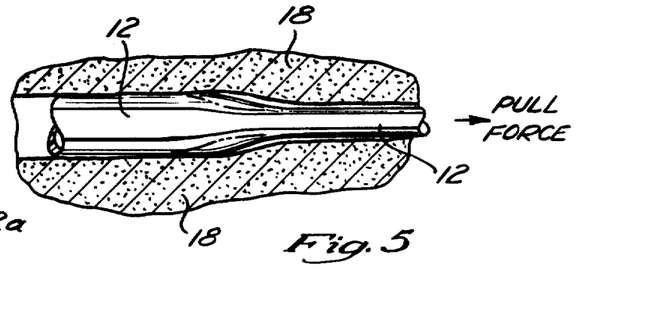
FIG. 5 is a schematic drawing showing the drain of the present invention progressively decreasing in cross-sectional area along its length, as a tensile force is applied thereto, and showing such decrease in cross-sectional area relieving the gripping force of the tissue on the drain to permit the drain to be removed from the wound more easily.

The fluted drain 12 of the present invention is uniform in cross-section throughout its length to eliminate stress raisers or weak points in the drain 12. Further, the drain 12 is preferably made from a highly biocompatible elastomer, such as silicone, having a durometer shore in the range of 40 to 70 shore A. This makes the drain 12 very soft and pliable, particularly at the lower end of the range, to reduce patient discomfort and irritation of the wound 18 (FIG. 1), while providing sufficient rigidity for added kink resistance. Moreover, this durometer shore rating permits the drain 12 to reduce in cross-sectional area when a relatively small pulling force is applied to remove the drain 12 from the wound 18. This characteristic of the drain 12 is illustrated in FIG. 5, which shows the drain 12 decreasing in cross-sectional area as the surgeon applies a pulling force thereto. Such decrease in cross-sectional area begins at the end of the drain 12 closest to the body opening 20 (FIG. 1) and progressively continues, as shown in phantom lines in FIG. 5, throughout the length of the drain 12. This relieves the gripping force of the tissue, and thereby makes the drain 12 easier to extract from the patient, reduces the risk of damage to the tissues surrounding the wound 18, and reduces the risk of drain breakage.

The drain 12 is preferably radially symmetrical. As used herein, radially symmetrical means that for plural, equiangular radii extending from a central longitudinal axis, the number of such plural radii being equal to the number of drain lumens, there are corresponding parts of the drain on each of said plural radii, regardless of the orientation of such equiangular radii about such central axis, and regardless of the distance of such corresponding parts from the central axis. In the case of the drain 12, such corresponding parts of the drain will, additionally, be equidistant from the central axis, since the drain 12 is round. Such radial symmetry permits the drain to decrease in cross-sectional area uniformly along each of the plural radii, thereby reducing any tendency of the drain to twist in the wound as the drain is pulled therefrom. Further, such symmetry permits the drain to lie in the wound in any orientation and to drain from openings spaced equiangularly around its periphery for increased effectiveness. Moreover, it makes the compressive strength of the drain uniform along such radii.

Figures 7, 8, 9:
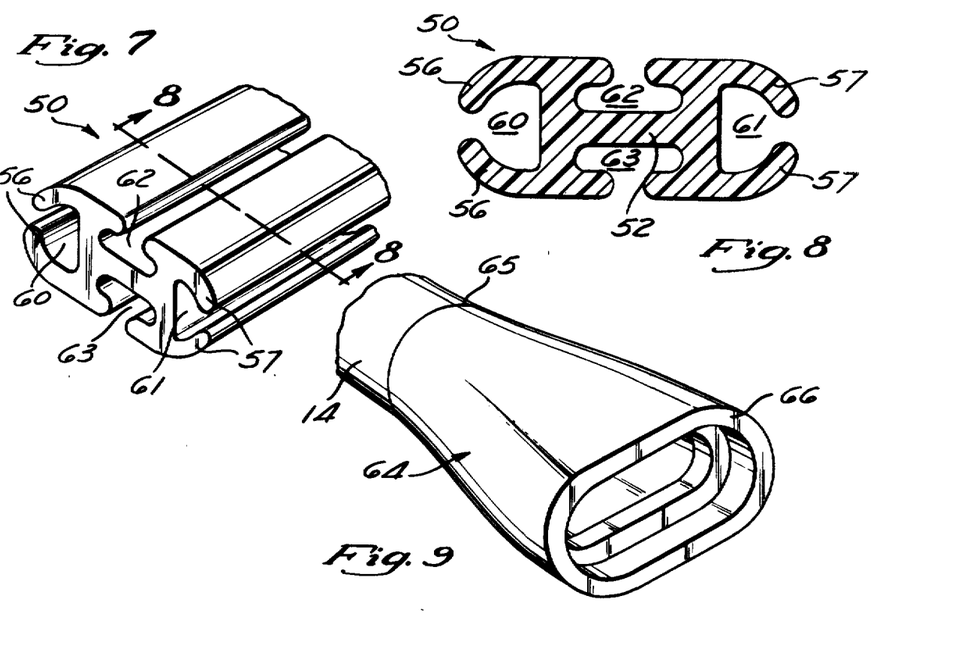
FIG. 7 is a partial perspective view of a second embodiment of the present invention showing a four-lumen oval or flat drain.
FIG. 8 is a cross-sectional view of the drain of the second embodiment taken along lines 8—8 of FIG. 7.
FIG. 9 is a perspective view of a tubular collar for connecting the drain of FIGS. 7 and 8 to an overflow tube.

The ends of the drain 12 and outflow tube 14 may be connected together in abutting relationship by means of a flexible tubular collar 40, as shown in FIG. 7. This collar 40 spans the butt joint 39 and may be affixed to the drain 12 and tube 14 by a suitable adhesive material. However, in applying the adhesive, care must be exercised to prevent the adhesive from clogging the lumens 38. Preferably, the ends of the collar 40 are gently tapered towards the outer walls of the drain 12 and tube 14 to eliminate any projections which may cause tissue damage during removal of the catheter 10. Although the butt-type joint 39 is not essential, it is preferable, since it provides added strength and kink resistance at the connection. However, the butt joint 39 may tend to block the ends of the lumens 38 (FIGS. 2 and 3), and thus restrict fluid flow from the lumens 38 into the tube 14. To prevent this from occurring, a portion of the core 30 is removed by forming a semi-spherical cutout or recess 42 in the abutting end of the drain 12, thereby permitting fluid communication between the lumens 38 (FIGS. 2 and 3) and the semi-spherical recess 42. Thus, even if the butt joint 39 blocks fluid flow through the end of the lumens 38, the recess 42 provides an unrestricted flow path which permits fluid to travel from the lumens 38 into the recess 42, and from the recess 42 into the outflow tube 14.

To insure a bond of sufficient strength between the tubular collar 40 and the drain 12, it is crucial that the overhang portions 34 conform to the interior wall of the collar 40 to permit contact therewith throughout a substantial portion thereof. In the embodiment described above, the overhang portions 34 contact the interior wall of the collar 40 through 75 to 80 percent of its circumference. The precise percentage of circumferential contact will, of course, vary, depending on the width of the grooves 38. However, such percentage should be at least 50 percent to insure an adequate bond between the collar 40 and drain 12.

In contrast to the round cross-sectional contour of the drain 12, a second embodiment of the present invention provides a drain 50 with an oval cross-sectional contour, as shown in FIGS. 7 and 8. Unless otherwise indicated, the term "closed curve" will be used generically as referring to any contour which will cooperate with the inside surface of a mating tube, such as the tubular collar 40. The drain 50 preferably is also radially symmetrical. However, since the drain 50 is oval, rather than round, the corresponding parts of the drain, referred to in the above definition of radial symmetry, will not be equidistant from the central axis. Thus, although both the drains 12,50 are radially symmetrical, the drain 50 differs from the drain 12 in this respect. The drain 50 also has diametrical symmetry, which, as used herein, means that for opposed radii (i.e., 180 degrees relative to each other) extending from a central axis, there are corresponding parts of the drain on such radii, equidistant from the central axis, regardless of the orientation of such radii about the axis. Of course, the drain 12 of the first embodiment also has diametric symmetry. Such symmetry has many of the same advantages as radial symmetry.

The drain 50 functions in the same manner as the drain 12. Further, the drain 50, like the drain 12, is specifically designed for use in draining closed, deep wounds. However, the oval or flat configuration of the drain 50 makes it particularly useful for draining areas between organs, or other areas where surgeons typically prefer drains having an oval or flat profile.

The drain 50 comprises a central strut or core portion 52 perpendicularly connected at its ends to respective side strut portions 54,55. Respective overhang portions 56 are connected to each of the ends of the side strut portion 54. Similarly, respective overhang portions 57 are connected to each of the ends of the side strut portion 55. The struts 54,55 and overhang portions 56,57 form plural T-shaped members radiating from the core 52. As best seen in FIG. 8, the two pairs of overhang portions 56,57, respectively, cooperate to form a segmented oval. Further, like the overhang portions 34 of the drain 12, the overhang portions 56,57 of the drain 50 form longitudinal grooves 58 (FIG. 7) throughout the length of the drain 50. The pair of overhang portions 56 extend arcuately from the strut portion 54 and cooperate with the outer wall of the strut portion 54 to form an essentially semi-circular lumen 60. In like manner, the pair of overhang portions 57 extend arcuately from the strut portion 55 and cooperate with the outer wall of the strut portion 55 to form a second, essentially semi-circular, lumen 61, in opposed relationship to the lumen 60. Additionally, the overhang portions 56,57 extend on either side of the central strut portion 52, in parallel relationship thereto, to form a pair of essentially rectangular lumens 62,63 on opposite sides of the central strut portion 52. Thus, viewed from the perspective of FIGS. 7 and 8, the drain 50 has two side lumens 60,61, a top lumen 62, and a bottom lumen 63. Further, each of the lumens 60,61,62,63 has a respective longitudinal groove 58 for fluid communication with the wound. Therefore, drainage is provided from each of four sides of the drain 50.

Figure 6:
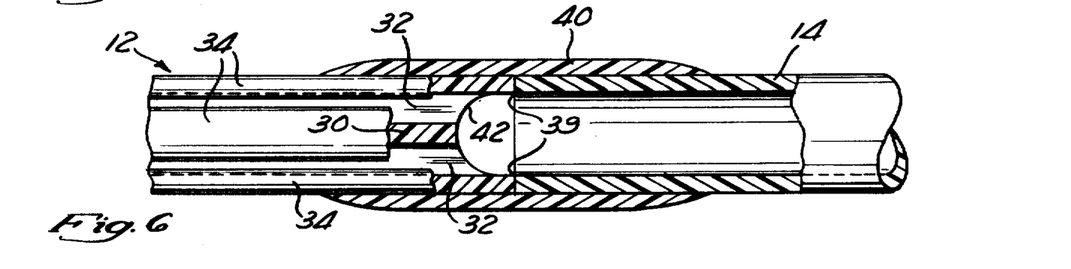
FIG. 6 is an elevation view in partial cross-section of the drain of the present invention, connected in abutting relationship to an outflow tube by a tubular collar, showing the semi-spherical recess for providing fluid communication between the drain and outflow tube.

The drain 50 may be connected to an outflow tube by providing a suitable connector, formed in accordance with the teachings discussed in reference to FIG. 6. For example, referring to FIG. 9, a tubular collar 64 is adapted at one end 65 for connection to a round outflow tube 14 and at the other end 66 for connection to the oval drain 50. An annular flange 67, projecting inwardly from, and perpendicular to, the interior surface of the tubular collar 64, is provided a short distance from the end 66. The portion of the collar 64 between the flange 67 and end 66 is sized to receive the drain 50. Further, the portion of the collar 64 between the annular flange 67 and end 65 is tapered to provide a smooth transition between the drain 50 and tube 14. When the drain 50 is inserted into the collar 64, the annular flange 67 prevents the drain 50 from extending into, and thus, being squeezed by, the tapered transition portion of the collar 64. This prevents the ends of the lumens 60,61,62,63 from being accidentally closed when the catheter is assembled. However, it is possible that the flange 67 may block the ends of the lumens 60,61,62,63 in the same manner that the butt joint 39 (FIG. 6) may block the lumens 38 of the drain 12. Accordingly, it is preferable to provide a recess (not shown) in the end of the drain 50, formed according to the teachings discussed in reference to the recess 42 of FIG. 6. This recess functions in the same manner as the recess 42 to permit fluid communication between the drain 50 and tube 42, even if the lumens 60,61,62,63 are blocked by the flange 67. As an alternative to this recess, the flange 67 may be provided with slots (not shown) which are oriented to align with the lumens 60,61,62,63, respectively, and thus, provide a flow path from one side of the flange 67 to the other.

The drain 50, as well as the drain 12 (FIGS. 2 and 3), may be formed in one step by well known extrusion processes. Thus, the drains 12,50 of the present invention may be manufactured at less cost than perforated drains.

A drain constructed in accordance with FIGS. 1 to 9 provides approximately twice the tissue contact drainage area, twice the lumenal flow drainage area, and twice the tensile strength of comparable prior art perforated drains. Further, it substantially reduces patient discomfort, wound irritation, and tissue damage, particularly during removal of the drain. Moreover, this drain is safer and more reliable than comparable prior art drains, and may advantageously be manufactured from highly biocompatible material by a relatively low cost, one-step extrusion process. Thus, the drain of the present invention provides significant advances with respect to wound drain catheters for closed, deep wounds.

Figure 10:
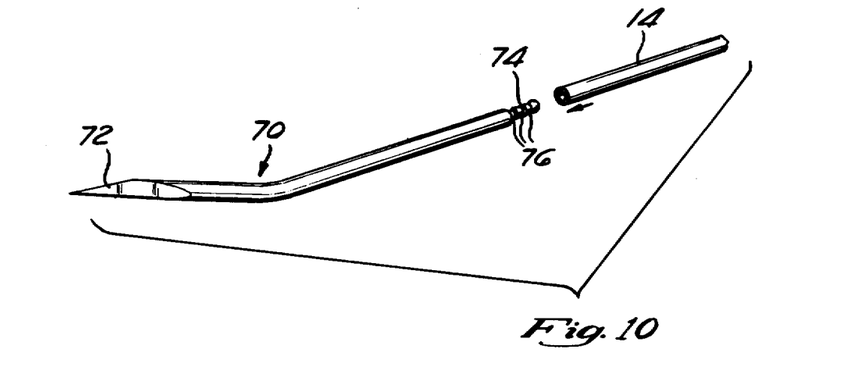
FIG. 10 is a perspective view of a trocar and a portion of an outflow tube, positioned for attachment to the trocar.

Referring to FIG. 10, it is preferable, although not essential, to insert the catheter 10 (FIG. 1) in the patient's body by means of a trocar 70. The trocar 70 is a rod-shaped, stainless steel, surgical instrument having a blade portion 72 at one end and a connector portion 74 at the other end. The connector portion 74 has plural annular ridges 76 which grippingly engage the interior wall of the outflow tube 14 to attach the trocar 70 and tube 14 together. However, as previously mentioned, this method of attachment has proven to be unsatisfactory for use with a silicone outflow tube 14, since the outflow tube 14 is often separated from the trocar 70 when the connector portion is passed through body tissue. Accordingly, the present invention includes an improved method for attaching the trocar 70 to the outflow tube 14.

Although the outflow tube 14, discussed in reference to FIG. 10, is described as being made from silicone, it will be understood that the outflow tube 14, as discussed in reference to other drawings, may be formed from materials other than silicone.

Figure 11:
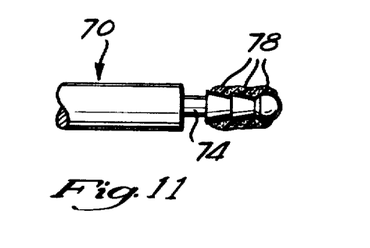
FIG. 11 is an elevation view of the trocar showing its annular ridges coated with a silicone sealant.
Figure 12:
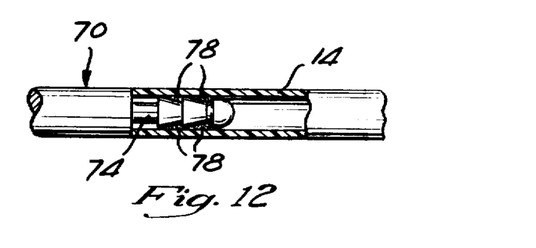
FIG. 12 is an elevation view in partial cross-section of the connector portion of the trocar with sealant applied thereto, and the end portion of an outflow tube connected together, illustrating the improved method for attaching the trocar to the outflow tube.

The improved method of attachment involves coating the connector portion 74 with a primer 77 (FIG. 11) which creates a bonding surface compatible with both stainless steel and silicone. Such a primer 77 is commercially available from Hughson Chemicals, Lord Corporation, Erie, Pa., under the name Chemlok ®, manufacturer's designation V-B-311-312/Primer/(40G)/PI. After coating the connector portion 74 with the primer 77, the spaces between the annular ridges 76 are filled with a silicone adhesive sealant 78, as shown in FIG. 11. The sealant filler 78 is commercially available as RTV Silicon Rubber Adhesive Sealant, manufactured by General Electric Company, Waterford, N.Y. The silicone outflow tube 14 is then inserted onto the connector portion 74, as shown in FIG. 12. The sealant filler 78 provides a contact surface between the tube 14 and connector portion 74 throughout the length of the connector portion 74, and thus creates an extremely strong bond between the tube 14 and trocar 70. The foregoing method of attachment, therefore, substantially reduces the risk that the outflow tube 14 may separate from the trocar 70 when the connector portion 74 passes through tissue, and thus reduces the risk of procedure complications and injury to the patient.

What is claimed is:

1. A wound drain catheter for draining fluid form, or supplying medication to, a closed, deep wound, comprising:
    a drain comprising:
        a core portion having a longitudinal axis;
        plural strut portions extending outwardly from said core portion; and
        plural overhang portions, connected to the outward ends of said strut portions, respectively, said overhang portions cooperating with said strut portions to form plural longitudinal lumens, said overhang portions cooperating with each other to form, on the outer surface of said drain, the segments of a segmented, closed curve, the gaps between said segments providing plural longitudinal grooves for fluid communication between the wound and a respective one of said plural lumens, said grooves sized to inhibit tissue from growing therein and debris from passing therethrough;
    said drain formed of a material which, when placed in tension between the gripping wound tissue and a force used to withdraw said drain from said wound, will reduce sufficiently in cross-section to reduce said gripping force to facilitate withdrawal; said drain having a substantially uniform cross section throughout the portion of its' length which is placed in tension during such removal to provide means for reducing stress risers and thus preventing breakage;
    a flexible outflow tube having a smooth exterior for sealing to surface tissue at the point of exit from a patient's body; and
    means conforming to said segmented, closed curve, for connecting said outflow tube to said drain.

2. A wound drain catheter, as defined in claim 1, wherein said plural struts combine with respective plural overhang portions to form plural T-shaped members.

3. A wound drain catheter for draining fluid from, or supplying medication to, a closed, deep wound, comprising:
    a drain, comprising:
        a core portion having a longitudinal axis;
        plural strut portions extending outwardly from said core portion; and
        plural overhang portions, connected to the outward ends of said strut portions, respectively, said overhang portions cooperating with said strut portions to form plural longitudinal lumens, said overhang portions cooperating with each other to form, on the outer surface of said drain, the segments of a segmented, closed curve, the gaps between said segments providing plural longitudinal grooves for fluid communication between the wound and respective one of said plural lumens, said grooves sized to inhibit tissue from growing therein and debris from passing therethrough;
    a flexible outflow tube having a smooth exterior for sealing to surface tissue at the point of exit from a patient's body; and
    means conforming to said segmented, closed curve, for connecting said outflow tube to said drain;
    wherein said outflow tube and said drain are connected end-to-end in abutting relationship, and wherein the connected end of said drain includes a recess in said core portion, said recess providing fluid communication between said lumens and said recess to permit fluid flow between said drain and said tube.

4. A wound drain catheter, as defined in claim 1, wherein said connecting means comprises a collar, and wherein the outer surfaces of said overhang portions contact the interior wall of said collar through at least 50 percent of the circumference of said collar.

5. A wound drain catheter, as defined in claim 1, wherein said drain has at least four strut portions extending from said core portion.

6. A wound drain catheter, as defined in claim 1, wherein said plural strut portions project radially from said core portion at equal angles relative to each other.

7. A wound drain catheter, as defined in claim 1, wherein said drain is uniform in cross-section throughout its length.

8. A wound drain catheter, as defined in claim 1, wherein said longitudinal grooves are parallel to said longitudinal axis.

9. A wound drain catheter, as defined in claim 1, wherein said drain is radially symmetrical.

10. A wound drain catheter, as defined in claim 9, wherein said radially symmetrical drain has corresponding portions of said drain on each of equi-angular, plural radii extending from said central axis, and said corresponding portions are equi-distant from said central axis.

11. A wound drain catheter, as defined in claim 1, wherein said drain has diametrical symmetry.

12. A wound drain catheter, as defined in claim 1, wherein said closed curve is a circle.

13. A wound drain catheter, as defined in claim 1, wherein said closed curve is an oval.

14. A wound drain catheter for draining fluid from, or supplying medication to, a closed, deep wound, comprising:
    a flexible silicone drain having plural, external, longitudinal grooves extending along a major portion of the length of said drain, said grooves forming lumens for said drain, said drain having a smooth external surface between said grooves and formed of a material which will reduce sufficiently in cross-section in response to longitudinal tension to permit said drain to contract away from wound tissue as said drain is pulled from said wound, said drain having a substantially uniform cross-section throughout the portion of the length which is placed in tension during removal to provide means for reducing stress risers and thus preventing breakage of said drain;
    a flexible outflow tube in fluid communication with said grooves and having a smooth exterior for sealing to surface tissue at the point of exit from a patient's body; and
    a connector for attaching said drain to said outflow tube securely enough to permit said drain to be withdrawn from said wound by pulling on said outflow tube.

15. A wound drain catheter, as defined in claim 14, wherein said silicone drain has a durometer shore between 40 and 70 shore A.

16. A wound drain catheter, as defined in claim 14, wherein said connector comprises a tube which has a flange which abuts one end of said drain, and said drain comprises a recess for providing a fluid pathway between said drain and said outflow tube.

17. A wound drain catheter, as defined in claim 14, wherein said drain is formed of silicone which is sufficiently elastic to cause said drain to reduce in cross-sectional area by at least 30 percent in response to a tensile force of two pounds to facilitate withdrawal of the drain.

18. A wound drain catheter for draining fluid from, or supplying medication to, a closed, deep wound, comprising:
   a drain, made from material having a durometer shore of from 40 to 70 Shore A, to permit said drain to shrink away from the wound during withdrawal, thereby facilitating withdrawal of the drain, comprising:
      a core; and
      at least three T-shaped members projecting from said core, and cooperating to form (i) at least three lumens, and (ii) at least three grooves for providing fluid communication between the wound and said lumens, said grooves sized to inhibit tissue from growing therein or debris from passing therethrough said core and T-shaped members having a uniform cross section to provide a means for reducing stress risers and thereby prohibit breakage during said withdrawal; and
   a flexible outflow tube having a smooth exterior for sealing to surface tissue at a point of exit from a patient's body, one end of said outflow tube providing means for connecting said catheter to a suction level, and the other end of said outflow tube providing means for connecting said outflow tube to said drain.

19. A drain, as defined in claim 18, wherein said plural T-shaped members are of equal size and project equiangularly from said core.

20. A method of drawing or supplying medication to a closed, deep wound, comprising:
   providing a drain having plural, external, grooves extending along a major portion of the length of said drain, said grooves forming lumens for said drain, said drain having a smooth external surface between said grooves and having a substantially uniform cross-section substantially free of stress risers, made from a silicone elastomer having a durometer shore of from 40 to 70 shore A, said drain preattached to an outflow tube which is in fluid communication with said grooves;
   placing said drain and a portion of said outflow tube in said wound;
   closing said wound to seal it from the atmosphere;
   connecting said outflow tube to a reservoir; and
   removing said drain from said wound by applying a tensile force thereto, said tensile force causing said drain to decrease in cross-sectional area to reduce the gripping force of tissue surrounding the drain, said substantially uniform cross section providing means for preventing breakage of said drain during removal.

21. A method of manufacturing a wound drain catheter for closed, deep wounds, comprising:
   constructing a drain by:
      selecting a material which responds to a longitudinal tension by reducing in cross-section sufficiently to contract away from wound tissue as said drain is pulled from said wound, thereby facilitating withdrawal of said drain, said drain having a substantially uniform cross-section substantially free of stress risers along the reducing portion of said drain to provide means for prohibiting breakage of said drain;
      forming a central core portion and at least three T-shaped members, each projecting from said core portion, cooperating to form at least three lumens, each having a respective longitudinal groove for fluid communication with the wound, said grooves sized to inhibit tissue from growing therein and debris from passing therethrough; and
      attaching said drain to a flexible outflow tube having a smooth exterior for sealing to surface tissue at the point of exit from the patient's body in a manner which will permit withdrawal of said withdrawal of said drain from deep wounds through application of tensile force on said outflow tube.

22. A method of manufacturing a wound drain catheter, as defined in claim 21, wherein the step of constructing said drain additionally comprises:
   forming a recess in the end of said drain most distal from said wound to permit fluid communication between said at least three lumens and said recess.

23. A method of manufacturing a wound drain catheter, as defined in claim 21, wherein said uniform cross-section drain is made from a material having sufficient elasticity to cause said drain to reduce in cross-sectional area by at least 30 percent when a two pound tensile force is applied thereto to reduce the gripping force of the tissue surrounding said drain during removal of said drain from the wound.

24. A method of manufacturing a wound drain catheter, as defined in claim 21, wherein said drain is made from a silicone material having a durometer shore between 40 and 70 shore A.

25. A method of manufacturing a wound drain catheter, as defined in claim 21, wherein said drain has four said T-shaped members.

26. A method of attaching a trocar to a silicone outflow tube, comprising:
   coating the connector portion of said trocar with a primer which creates a bonding surface compatible with both stainless steel and silicone;
   filling irregularities on the connector portion of said trocar with a silicone adhesive sealant; and
   inserting said outflow tube on the connector portion of said trocar.

27. A wound drain catheter for draining fluid from, or supplying medication to, a closed, deep wound in a patient, said catheter comprising:
   a drain having plural, external, longitudinal grooves extending along a major portion of the length of said drain, said grooves forming lumens for said drain, said drain having a smooth external surface between said grooves; and
   an outflow tube, in fluid communication with said grooves and connected to said drain so that the direction of fluid flow in the drain and the outflow tube is the same, said outflow tube having a smooth exterior surface for sealing to surface tissue at the point of exit from the patient's body, said drain having a uniform cross-section along its length and being formed of flexible material so that pulling the drain from the patient causes a reduction in cross-sectional area of the drain to relieve the gripping force of the patient's tissue on the drain, said uniform cross section providing means for reducing stress risers and thereby eliminating breakage of said drain due to said pulling.

28. A wound drain catheter, as defined in claim 27, wherein said drain is formed of silicone which is sufficiently elastic to cause said drain to reduce in cross-sectional area by at least 30 percent in response to a tensile pulling force of two pounds.

29. A wound drain catheter, as defined in claim 27, wherein said drain has a durometer shore hardness between 40 and 70 shore A.

30. A wound drain catheter for draining fluid from, or supply medication to, a closed, deep wound, comprising:
    a drain formed of a material which will reduce sufficiently in cross-section in response to longitudinal tension to permit said drain to contract away from wound tissue as said drain is pulled from said wound, said drain having a cross-section substantially free of stress risers along the reduced length of said drain, comprising:
        a core portion having a longitudinal axis;
        plural strut portions extending outwardly from said core portion; and
        plural overhang portions, connected to the outward ends of said strut portions, respectively, said overhang portions cooperating with said strut portions to form plural longitudinal lumens, said overhang portions cooperating with each other to form, on the outer surface of said drain, the segments of a segmented, closed curve, the gaps between said segments providing plural longitudinal grooves for fluid communication between the wound and a respective one of said plural lumens, said grooves sized to inhibit tissue from growing therein and debris from passing therethrough;
    a flexible outflow tube having a smooth exterior for sealing to surface tissue at the point of exit from a patient's body; and
    means conforming to said segmented, closed curve, for connecting said outflow tube to said drain.

31. A wound drain catheter for draining fluid from, or supplying medication to, a closed, deep wound, comprising:
    a flexible silicone drain having a substantially uniform cross section and formed of material which will reduce sufficiently in cross section during removal of said drain to contract away from wound tissue, said substantially uniform cross section reducing the susceptibility of said drain to breakage, comprising:
        a core; and
        at least three T-shaped members projecting from said core, and cooperating to form (i) at least three lumens, and (ii) at least three grooves for providing fluid communication between the wound and said lumens, said grooves sized to inhibit tissue from growing therein or debris from passing therethrough; said lumens cooperating to provide an effective drain even when said drain is kinked or squeezed; and
    a flexible outflow tube having a smooth exterior for sealing to surface tissue at a point of exit from a patient's body, one end of said outflow tube providing means for connecting said catheter to a suction device, and the other end of said outflow tube providing means for connecting said outflow tube to said drain.

32. A wound drain catheter for draining fluid from, or supplying medication to, a closed, deep wound, comprising:
    a flexible silicone drain having plural, external, longitudinal grooves extending along a major portion of the length of said drain, said grooves forming lumens for said drain, said drain having a smooth external surface between said grooves and formed of a material which will reduce sufficiently in cross-section to reduce the gripping force exerted by wound tissue on said drain, when said drain is placed in tension by said gripping force and a force used to withdraw said drain from the wound, said drain having a substantially uniform cross section to provide means for reducing stress risers and thereby preventing breakage during withdrawal;
    a flexible outflow tube in fluid communication with said grooves and having a smooth exterior for sealing to surface tissue at the point of exit from a patient's body; and
    means for attaching said drain to said outflow tube securely enough to permit said drain to be withdrawn from said wound by pulling on said outflow tube.

* * * * *